United States Patent
Kobayashi et al.

(10) Patent No.: US 7,033,744 B2
(45) Date of Patent: *Apr. 25, 2006

(54) METHOD FOR PROLIFERATING A LIVER CELL, A LIVER CELL OBTAINED THEREBY, AND USE THEREOF

(76) Inventors: Naoya Kobayashi, 2033-15, Miyoshi, Okayama-shi, Okayama 703-8261 (JP); Philippe Leboulch, 137 8th St., Charlestown, MA (US) 02129; Noriaki Tanaka, 2325-1, Rokujoinnaka, Kamogata-cho, Asakuchi-gun, Okayama 719-0252 (JP); Toshiyoshi Fujiwara, 3-5-30, Higashiyama, Okayama-shi, Okayama 703-8281 (JP); Toshinori Totsugawa, 2374, Nagawa, Seto-cho, Fukuyama-shi, Hiroshima 720-0836 (JP)

( * ) Notice: Subject to any disclaimer, the term of this patent is extended or adjusted under 35 U.S.C. 154(b) by 266 days.

This patent is subject to a terminal disclaimer.

(21) Appl. No.: 10/169,085

(22) PCT Filed: Mar. 15, 2002

(86) PCT No.: PCT/US02/06639

§ 371 (c)(1),
(2), (4) Date: Jan. 6, 2003

(87) PCT Pub. No.: WO02/074968

PCT Pub. Date: Sep. 26, 2002

(65) Prior Publication Data

US 2004/0033215 A1 Feb. 19, 2004

(51) Int. Cl.
*A01N 1/00* (2006.01)

(52) U.S. Cl. .................. 435/1.1; 435/462; 435/370

(58) Field of Classification Search .............. 435/1.1, 435/462, 370
See application file for complete search history.

(56) References Cited

PUBLICATIONS

J. Nakayama, "Telomerase activation by hTRT in human normal fibroblasts and hepatocellular carcinomas", *Nature Genetics*, vol. 18 (Jan. 1998) pp. 65–68.
K. Nagao, "Telomerase reverse transcriptase mRNA expression and telomerase activity in hepatocellular carcinoma", *Journal of Gastroenterology* (1999) pp. 83–87.
K.A. Westerman, et al; "Reversible immortalization of mammalian cells mediated by retroviral transfer and site–specific recombination"; Proc. Natl. Acad. Sci. USA; vol. 93, pp. 8971–8976; Aug. 1996; Cell Biology.
Jin Cai, et al; "Construction of a non–tumorigenic rat hepatocyte cell line for transplantation: reversal of hepatocyte immortalization by site–specific excision of the SV40 T antigen"; Journal of Hepatology 2000; 33: 701–708.
Naoya Kobayashi, et al; "Efficient Cre/loxP Site–Specific Recombination in a HepG2 Human Liver Cell Line"; Cell Transplantation, vol. 9, pp. 737–742, 2000.

*Primary Examiner*—James Ketter
(74) *Attorney, Agent, or Firm*—Armstrong, Kratz, Quintos, Hanson & Brooks, LLP

(57) ABSTRACT

The present invention provides a method comprising a step of transferring a cell proliferation factor gene into a mammalian liver cell to obtain an immortalized liver cell, a step of proliferating the immortalized liver cell, and a step of removing the cell proliferation factor gene from the immortalized liver cell; a large number of liver cells obtained thereby; and a treating agent and a artificial liver comprising obtained liver cell.

22 Claims, 4 Drawing Sheets

SEQUENCE LISTING

<160> NUMBER OF SEQ ID NOS: 24

<210> SEQ ID NO 1
<211> LENGTH: 34
<212> TYPE: DNA
<213> ORGANISM: P1 phage
<220> FEATURE:
<223> OTHER INFORMATION: LoxP sequence

<400> SEQUENCE: 1
ataacttcgt atagcataca ttatacgaag ttat                    34

<210> SEQ ID NO 2
<211> LENGTH: 20
<212> TYPE: DNA
<213> ORGANISM: Artificial Sequence
<220> FEATURE:
<223> OTHER INFORMATION: 5' primer for polymerase chain reaction to
      detect Albumin gene

<400> SEQUENCE: 2
aaacctcttg tggaagagcc                                    20

<210> SEQ ID NO 3
<211> LENGTH: 20
<212> TYPE: DNA
<213> ORGANISM: Artificial Sequence
<220> FEATURE:
<223> OTHER INFORMATION: 3' primer for polymerase chain reaction to
      detect Albumin gene

<400> SEQUENCE: 3
caaagcaggt ctccttatcg                                    20

<210> SEQ ID NO 4
<211> LENGTH: 20
<212> TYPE: DNA
<213> ORGANISM: Artificial Sequence
<220> FEATURE:
<223> OTHER INFORMATION: 5' primer for polymerase chain reaction to
      detect ASGPR gene

<400> SEQUENCE: 4
taggagccaa gctggagaaa                                    20

<210> SEQ ID NO 5
<211> LENGTH: 20
<212> TYPE: DNA
<213> ORGANISM: Artificial Sequence
<220> FEATURE:
<223> OTHER INFORMATION: 3' primer for polymerase chain reaction to
      detect ASGPR gene

<400> SEQUENCE: 5
acctgcaggc agaagtcatc                                    20

<210> SEQ ID NO 6
<211> LENGTH: 20
<212> TYPE: DNA
<213> ORGANISM: Artificial Sequence
<220> FEATURE:
<223> OTHER INFORMATION: 5' primer for polymerase chain reaction to
      detect Bilirubin-UGT gene

<400> SEQUENCE: 6
atgacccgtg cctttatcac                                                20

<210> SEQ ID NO 7
<211> LENGTH: 20
<212> TYPE: DNA
<213> ORGANISM: Artificial Sequence
<220> FEATURE:
<223> OTHER INFORMATION: 3' primer for polymerase chain reaction to
      detect Bilirubin-UGT gene

<400> SEQUENCE: 7
tcttggattt gtgggctttc                                                20

<210> SEQ ID NO 8
<211> LENGTH: 20
<212> TYPE: DNA
<213> ORGANISM: Artificial Sequence
<220> FEATURE:
<223> OTHER INFORMATION: 5' primer for polymerase chain reaction to
      detect CYP3A4 gene

<400> SEQUENCE: 8
ccaagctatg ctcttcaccg                                                20

<210> SEQ ID NO 9
<211> LENGTH: 20
<212> TYPE: DNA
<213> ORGANISM: Artificial Sequence
<220> FEATURE:
<223> OTHER INFORMATION: 3' primer for polymerase chain reaction to
      detect CYP3A4 gene

<400> SEQUENCE: 9
tcaggctcca cttacggtgc                                                20

<210> SEQ ID NO 10
<211> LENGTH: 20
<212> TYPE: DNA
<213> ORGANISM: Artificial Sequence
<220> FEATURE:
<223> OTHER INFORMATION: 5' primer for polymerase chain reaction to
      detect GK gene

<400> SEQUENCE: 10
atcaaacgga gagggactt                                                 20

<210> SEQ ID NO 11
<211> LENGTH: 20
<212> TYPE: DNA
<213> ORGANISM: Artificial Sequence
<220> FEATURE:
<223> OTHER INFORMATION: 3' primer for polymerase chain reaction to
      detect GK gene

<400> SEQUENCE: 11
agcgtgctca ggatgttgta                                                20

<210> SEQ ID NO 12
<211> LENGTH: 20
<212> TYPE: DNA
<213> ORGANISM: Artificial Sequence
<220> FEATURE:
<223> OTHER INFORMATION: 5' primer for polymerase chain reaction to
      detect GS gene

<400> SEQUENCE: 12
atgctggagt caagattgcg                                                20

<210> SEQ ID NO 13
<211> LENGTH: 20
<212> TYPE: DNA
<213> ORGANISM: Artificial Sequence
<220> FEATURE:
<223> OTHER INFORMATION: 3' primer for polymerase chain reaction to
      detect GS gene

<400> SEQUENCE: 13
tcattgagaa gacacgtgcg                                                  20

<210> SEQ ID NO 14
<211> LENGTH: 20
<212> TYPE: DNA
<213> ORGANISM: Artificial Sequence
<220> FEATURE:
<223> OTHER INFORMATION: 5' primer for polymerase chain reaction to
      detect GST-? gene

<400> SEQUENCE: 14
gccctacacc gtggtctatt                                                  20

<210> SEQ ID NO 15
<211> LENGTH: 20
<212> TYPE: DNA
<213> ORGANISM: Artificial Sequence
<220> FEATURE:
<223> OTHER INFORMATION: 3' primer for polymerase chain reaction to
      detect GST-? gene

<400> SEQUENCE: 15
ggctaggacc tcatggatca                                                  20

<210> SEQ ID NO 16
<211> LENGTH: 20
<212> TYPE: DNA
<213> ORGANISM: Artificial Sequence
<220> FEATURE:
<223> OTHER INFORMATION: 5' primer for polymerase chain reaction to
      detect human blood coagulation factor X gene

<400> SEQUENCE: 16
gtgcatggaa gagacctgct                                                  20

<210> SEQ ID NO 17
<211> LENGTH: 20
<212> TYPE: DNA
<213> ORGANISM: Artificial Sequence
<220> FEATURE:
<223> OTHER INFORMATION: 3' primer for polymerase chain reaction to
      detect human blood coagulation factor X gene

<400> SEQUENCE: 17
gaagtcaagc aggtcgaagg                                                  20

<210> SEQ ID NO 18
<211> LENGTH: 20
<212> TYPE: DNA
<213> ORGANISM: Artificial Sequence
<220> FEATURE:
<223> OTHER INFORMATION: 5' primer for polymerase chain reaction to
      detect hTERT gene

<400> SEQUENCE: 18
ctgaccaggg tcctattcca                                                  20

```
<210> SEQ ID NO 19
<211> LENGTH: 20
<212> TYPE: DNA
<213> ORGANISM: Artificial Sequence
<220> FEATURE:
<223> OTHER INFORMATION: 3' primer for polymerase chain reaction to
      detect hTERT gene

<400> SEQUENCE: 19
tggttatccc aagcaagagg                                                 20

<210> SEQ ID NO 20
<211> LENGTH: 30
<212> TYPE: DNA
<213> ORGANISM: Artificial Sequence
<220> FEATURE:
<223> OTHER INFORMATION: 5' primer for polymerase chain reaction to
      detect human ?-actin gene

<400> SEQUENCE: 20
tgacggggtc acccacactg tgcccatcta                                      30

<210> SEQ ID NO 21
<211> LENGTH: 30
<212> TYPE: DNA
<213> ORGANISM: Artificial Sequence
<220> FEATURE:
<223> OTHER INFORMATION: 3' primer for polymerase chain reaction to
      detect human ?-actin gene

<400> SEQUENCE: 21
ctagaagcat ttgcggtgga cgatggaggg                                      30

<210> SEQ ID NO 22
<211> LENGTH: 5
<212> TYPE: PRT
<213> ORGANISM: Artificial Sequence
<220> FEATURE:
<223> OTHER INFORMATION: Cell adhesion peptide

<400> SEQUENCE: 22

Gly Arg Gly Asp Ser
 1               5

<210> SEQ ID NO 23
<211> LENGTH: 4
<212> TYPE: PRT
<213> ORGANISM: Artificial Sequence
<220> FEATURE:
<223> OTHER INFORMATION: Cell adhesion peptide

<400> SEQUENCE: 23

Arg Gly Asp Ser
 1

<210> SEQ ID NO 24
<211> LENGTH: 11
<212> TYPE: PRT
<213> ORGANISM: human immunodeficiency virus type 1

<400> SEQUENCE: 24

Tyr Gly Arg Lys Lys Arg Arg Gln Arg Arg Arg
 1               5                  10
```

METHOD FOR PROLIFERATING A LIVER CELL, A LIVER CELL OBTAINED THEREBY, AND USE THEREOF

This application is a 371 National Stage application of PCT/US02/06639, filed Mar. 15, 2002, which claims priority under 35 U.S.C. 120 and 35 U.S.C. 365(c) of U.S.S.N. 09/809,187, filed Mar. 16, 2001.

TECHNICAL FIELD

The present invention relates to a method for proliferating a liver cell, a liver cell obtained thereby, and use thereof. In more detail, the present invention relates to the method for proliferating the liver cell using a gene engineering procedure, the in vitro liver cell obtained thereby, and use thereof such as a treating agent and an artificial liver.

BACKGROUND ART

Liver transplantation is the only treating method which can be utilized for patients with liver-based metabolic diseases or hepatic insufficiency. However, the treatment has problems such as shortage of donor livers, considerable postoperative lethality accompanied with operative risk, high costs and use of immunosuppressant over a long period. Recently, isolated hepatocyte transplantation or a bio-artificial liver with living hepatocytes is desired as filler until liver transplantation or regeneration of liver. Advantages of the isolated hepatocyte transplantation or the bio-artificial liver include that it is economical compared with an operation of liver transplantation, that the risk is few, and the like. In the isolated hepatocyte transplantation or the bio-artificial liver, a clinical use thereof is also limited because of the shortage of donor livers.

As an alternative to the isolated hepatocyte, there includes a liver cell-line which can be proliferated in large numbers in vitro, which maintains a property of the isolated hepatocyte and further which can provide a metabolic supplement after transplantation. It is expected that an establishment of the liver cell-line enabling to proliferate in large numbers and having a high-level liver function, and a development of a bank thereof enable the transplantation of required amount of liver cell as need arises and dissolve the shortage of donor livers.

It is known that a cell-line which maintains appropriate function for differentiation can be produced by transferring oncogenes to immortalize cells (K. A. Westerman, et al., Proc. Natl. Acad. Sci., USA., vol 93, 8971, (1996)). However, in case where the immortalized cell-line is infused into a living body or applied to a extracorporeal assist device such as the bio-artificial liver, there is possibility that a patient is exposed to unexpected risk of malignant transformation. It is not assured that the transplanted cell is finally rejected, even though a heterozoic cell or an incompatible homologous human cell is employed. In human, a stable chimera state with the heterozoic cell and accidental engraftment of HLA incompatible homologous tumor are reported (Gartner, et al., N. Eng. J. Med. Vol. 335, 1494, (1996); K. Paradis, et al., Science, vol. 285, 1236, (1999)). Therefore, it is desired that high-safety liver cells can be easily available in large scale.

In addition, in the aspect of other than purpose to treat liver-based diseases, needs for establishment of the normal liver cell-line enabling to proliferate in large numbers and the cell bank thereof is increased. Mainly, there include utilization for 1) an assay model for human drug metabolism, 2) a development of new drug, and 3) an infection model of human hepatitis.

However, in the conventional culture technique, it is difficult to proliferate the high-safety liver cells in large numbers.

In view of the above problem, the present invention purpose to provide a method for proliferating a mammalian liver cell, which enables the limitless proliferation. Moreover, the present invention purpose to provide a liver cell obtained by the said method, and use of the liver cell such as a treating agent and an artificial liver.

DESCLOSURE OF THE INVENTION

As a result of making an intensive study in view of the above problems, the present inventors have found the followings and completed the present invention. The present inventors have found that a large number of uniformal mammalian liver cell-lines can be obtained in vitro by removing a specific cell proliferation factor gene after a high-scale proliferation of an immortalized cell by transferring the gene.

That is to say, the present invention relate to a method for proliferating a liver cell in vitro which comprises a step of transferring a cell proliferation factor gene into a mammalian liver cell to obtain an immortalized liver cell, a step of proliferating the immortalized liver cell, and a step of removing the cell proliferation factor gene from the immortalized liver cell.

In the above method, the mammalian liver cell is preferably a human liver cell, more preferably a human adult liver cell.

In the above method, the cell proliferation factor gene is preferably hTERT (human telomerase reverse transcriptase) gene. Further, it is preferable that the cell proliferation factor gene is transferred using a retroviral vector.

In addition, in the above method the cell proliferation factor gene is preferably located between a pair of site-specific recombination sequences, the pair of site-specific recombination sequence is preferably LoxP sequence, further GFP (green fluorescence protein) preferably presents between the pair of site-specific recombination sequence.

In the above method, it is preferable that the immortalized liver cell is proliferated in serum-free medium.

In the above method, it is preferable that the cell proliferation factor gene is removed using a site-specific recombinase from the immortalized liver cell, that the site-specific recombinase is Cre recombinase, and further that the Cre recombinase is encoded by an adenoviral vector.

The present invention relates to an in vitro liver cell obtained by a method for proliferating a liver cell comprising a step of transferring a cell proliferation factor gene into a mammalian liver cell to obtain an immortalized liver cell, a step of proliferating the immortalized liver cell, and a step of removing the cell proliferation factor gene from the immortalized liver cell.

The in vitro liver cell obtained by the above method is preferably used as an assay model for drug metabolism in human liver.

The present invention relates to an agent for treating liver insufficiency, which comprises an in vitro liver cell obtained by a method for proliferating a liver cell comprising a step of transferring a cell proliferation factor gene into a mammalian liver cell to obtain an immortalized liver cell, a step of proliferating the immortalized liver cell, and a step of removing the cell proliferation factor gene from the immortalized liver cell.

Furthermore, the present invention relates to an artificial liver, which comprises an in vitro liver cell obtained by an in vitro method for proliferating a liver cell comprising a step of transferring a cell proliferation factor gene into a mammalian liver cell to obtain an immortalized liver cell, a step of proliferating the immortalized liver cell, and a step of removing the cell proliferation factor gene from the immortalized liver cell.

The above artificial liver preferably contains a microcarrier. The microcarrier is preferably cellulose bead, and the cellulose bead is preferably a cellulose bead whose surface is attached with a cell adhesion peptide. Moreover, it is most preferable that the microcarrier is a collagen microsphere. In addition, it is preferable that cell occupied rate on the microcarrier is in range of 80 to 100%.

The present invention also provides a method for preparing albumin comprising a step of cultivating an in vitro liver cell in serum free medium, the in vitro liver cell being obtained by the method comprising a step of transferring a cell proliferation factor gene into a mammalian liver cell, a step of proliferating the immortalized liver cell, and a step of removing the cell proliferation factor gene from the immortalized liver cell.

Furthermore, the present invention provides the above-mentioned method for proliferating a liver cell in vitro, wherein the step of obtaining an immortalized liver cell comprises a step of transferring a cell proliferation factor gene into a mammalian liver cell to obtain an immortalized liver cell, a step of transferring a DNA sequence encoding a site-specific recombinase at the downstream of a drug-induced promoter into the immortalized liver cell, and a step of obtaining an immortalized liver cell which expresses the site-specific recombinase depending on agent.

BEST MODE FOR CARRYING OUT THE INVENTION

Figure 1:
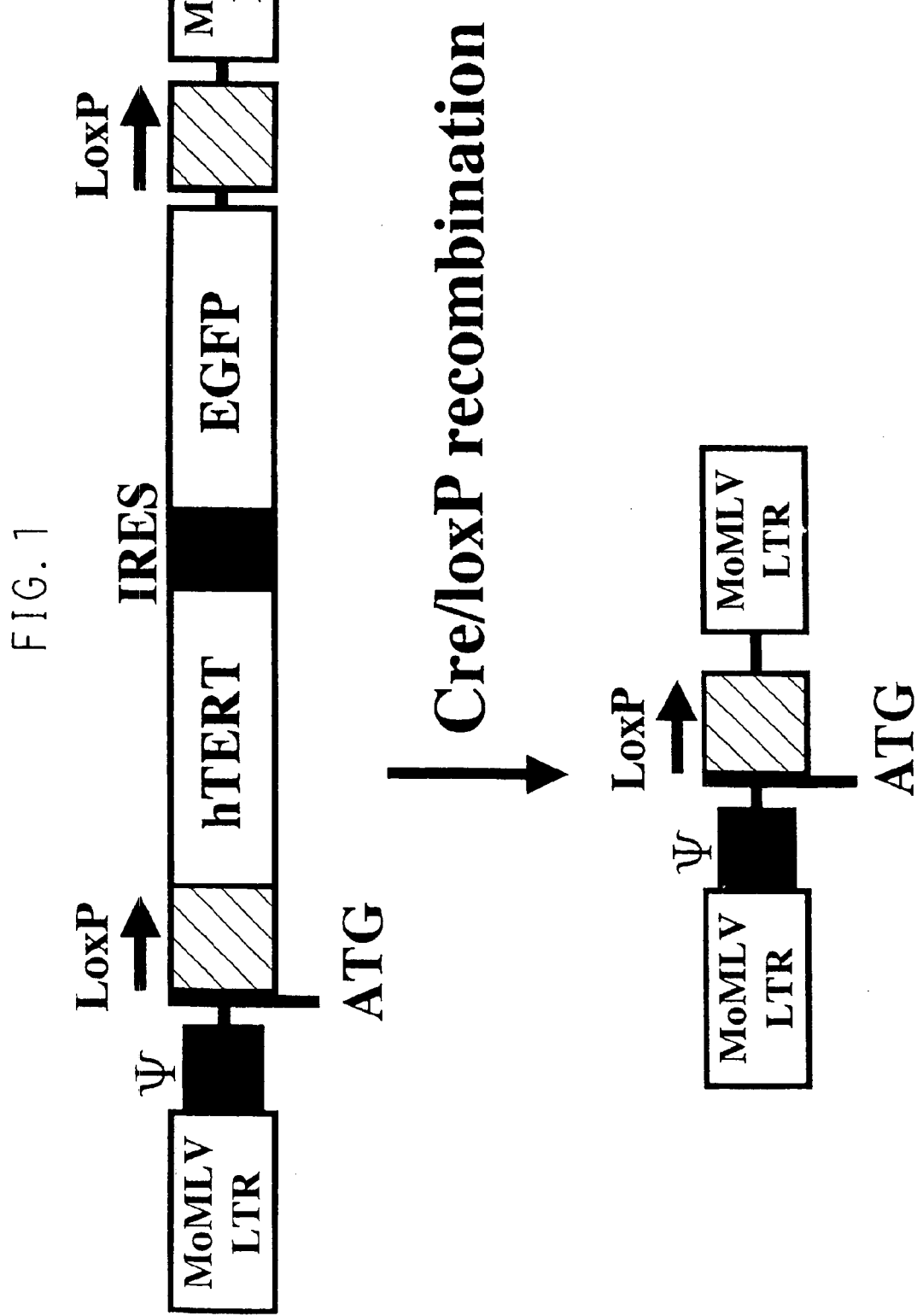
FIG. 1 shows specific excision mechanism to LoxP sequence by infecting adenoviral vector AxCANCre. Herein, ATG indicates starting codon, ψ packaging signal, LoxP LoxP sequence, hTERT hTERT gene, EGFP enhanced GFP gene, MoMLV LTR Moloney murine leukemia virus long terminal repeat, IRES encephalomyocarditis virus internal ribosome entry site, respectively.

As a mammalian liver cell employed in the present invention, there are liver cells of pig, monkey, anthropoid, human, and the like. Among them, the human liver cell is preferable, the human adult liver cell is the most preferable. The human embryo liver cell may also be applied. The term "liver cell" described herein means a cell having ability to produce protein such as albumin and various blood coagulation factors which are index of liver function, ability of gluconeogenesis, ability to produce carbamide, abilities of detoxication and purification of blood, and ability to metabolize amino acid, glucide and lipid. Examples thereof include hepatocyte, liver sinusoid endothelial cell, liver stellate cell, Pit cell, Kupffer cell and the like.

The cell proliferation factor gene employed in the present invention is provided from normal cell, and can immortalize a mammaliam liver cell by transferring. A product from the cell proliferation factor gene is those which essentially relates to cell proliferation and signal transfer in the normal cell. Examples thereof include those which function as growth factor, which have tyrosine kinase activity in the cell membrane, which bind to GTP in the interior of the cell membrane, which have serine/threonine kinase activity in the cytoplasm, and which have ability binding to DNA in the nucleus. Such cell proliferation factor gene includes ras gene, myc gene, hTERT gene or the like. The hTERT gene is preferable, because an expression of the hTERT gene is naturally enhanced in stem and progenitor cell of organs repeating regeneration over lifetime such as blood, skin, intestinal mucosa, endometrium and the like, and in lymphocyte which makes a clonal expansion each time it exposes to the specific antigen.

In accordance with the present invention, a retroviral vector is used for transferring the cell proliferation factor gene into the mammalian liver cell. The retroviral vector is used as means for transferring a foreign gene into an animal cell. Since the transferred gene is integrated into chromosomal DNA of the host cell, the gene is absolutely transmitted to the daughter cell, and therefore it is possible that the integrated gene is suitably expressed over long period.

As a process to transfer retroviral vectors, intravenous administration, intraperitoneal administration, intraportal administration and administration by direct puncture in case of in vivo, and a process by inoculating retroviral vectors directly on culture cells in case of in vitro are known. The intraportal administration and the administration by direct puncture and the process by direct inoculating are preferable.

As the process to transfer the retroviral vectors into the culture cells by inoculating the retroviral vectors directly on the culture cells, any process can be used as long as the process achieves the object of the present invention. For example, the transferring can be performed by culturing cells which produce the retroviral vectors, and then inoculating the resulting cultural supernatant on liver cells cultured separately. Various conditions such as culture condition and seeding density about each kind of cell can be determined according to the process well known in the art.

In addition, it is preferable that the inoculation on the culture cells is only once, considering effect on the cells, for example, stability of chromosomes. However, considering a transferring efficiency of the vectors, it is preferable that the time of the inoculation on the cells is more. Based on the facts, it is the most preferable in the present invention to perform 4-hour-infection twice a day, for 3 days in total.

Furthermore, the cell proliferation factor gene used in the present invention is located between a pair of site-specific recombinant sequences so that the gene can be excised later from pro-virus transferred into a liver cell. The "site-specific recombinant sequence" is a specific base sequences recognized by a site-specific recombinase, in between the sequences a DNA-strand excision, an exchange of strands and a coupling thereof are performed.

As the site-specific recombinant sequence, there is LoxP sequence, FRT sequence or the like. Among them, the LoxP sequence is preferable. The LoxP sequence is a sequence comprising 34 bases of "ATAACTTCGTATAGCATACAT-TATACGAAGTTAT" (SEQ ID NO: 1) for performing a homologous recombination by Cre recombinase alone. When a pair of LoxP sequence located in the same direction presents in a same DNA molecule, a DNA sequence located therebetween is excised to become a circular molecule (excision reaction). When each of the pair of LoxP sequences is located in different DNA molecules, respectively and one of the DNA molecules is a circular DNA, the circular DNA is inserted into the other DNA molecule using the LoxP sequence (insertion reaction).

Further, in the present invention, it is preferred that a selection marker such as GFP gene presents between the pair of site-specific recombinant sequences whenever the cell proliferation factor gene is transferred into the mammalian liver cell. "Between a pair of site-specific recombinant sequences" means a position located between the pair of site-specific recombinant sequences. The GFP gene is used to identify the liver cell selectively which is infected with the retroviral vector and wherein a pro-virus is integrated into genome, using FACS (fluorescence activated cell sorter). Therefore, if the liver cell wherein the pro-virus is integrated into genome is identified selectively, a drug-resistance gene can be used instead of the GFP gene.

As an example of the drug-resistance gene, there is hygromycin resistance gene, neomycin resistant gene, ampicillin resistance gene, *Escherichia coli* gpt gene or the like. It is not particularly limited thereto.

"Immortalized liver cell" described herein means a cell that is not tumorigenic, has a form like a normal liver cell, keeps liver-specific function relatively and has a characteristic that it grows in a short term without any special culture condition.

Concerning cultivation of the immortalized cell, it is preferable that cell-growth rate is fast. But it is more preferable that a special coating with collagen and the like on a surface of a culture vessel is not necessary, because it is easy to handle the vessel. A doubling time of the immortalized cell is from 24 to 72 hours, preferably from 24 to 48 hours, more preferably from 24 to 36 hours. Serum-free medium, which is supplemented with no serum derived from animal such as calf, is preferable for culture medium so that xenozoonosis is prevented. Serum-free medium is preferable for immortalized cells functionally to increase the production of albumin. CS-C medium is more preferable. CS-C medium doubling- or trebling-diluted with Dulbecco's modified Eagle medium (DMEM) may be used.

The immortalized liver cell herein used is a reversible immortalized cell which can be removed the transferred cell proliferation factor gene therefrom using the site-specific recombinase. The site-specific recombinase is an enzyme which recognizes the site-specific recombinant sequence specifically and performs a homologous recombination comprising an excision and coupling, independently. As the site-specific recombinase, there includes Cre recombinase, FLP recombinase or the like. Among them, the Cre recombinase is preferable. The Cre recominase is an enzyme which recognizes the LoxP sequence specifically.

The site-specific recombinase can be encoded by an expression vector such as an adenovirus vector or a plasmid vector. Alternatively, the site-specific recombinase may be fused with TAT protein derived from human immunodeficiency virus type 1(Green, M. and Loewenstein, P. M., Cell 55, p179–1188, 1988: Frankel, A. D. and Pabo, C. O., Cell 55, p1189–1193, 1988: Nagahara, H. et al., Nat. Med. 1988, 4, 1449–1452). A site-specific recombination reaction is caused in said immortalized cells by adding the fused protein to the culture medium, because TAT protein contains a protein transduction domain. Adenovirus vectors are cytotoxic. On purpose to prevent such risk, the site-specific recombinase is preferred either to be encoded by an expression vector other than an adenovirus vector or to be fused TAT protein.

The fused protein of a site-specific recombinase and TAT protein is not limited, as long as both the site-specific recombinase and a protein transduction domain of TAT protein (i.e. Tyr-Gly-Arg-Lys-Lys-Arg-Arg-Gln-Arg-Arg-Arg)(SEQ ID NO: 24) are comprised. The fused protein can induce a site-specific recombination reaction by addition thereof to the culture medium of said immortalized cells.

The expression vector used in the present invention is not specifically limited, as long as they contain a sequence encoding the site-specific recombinase. As a promoter for the site-specific recombinase, a drug-induced promoter is preferred. The "drug-induced promoter" herein means a promoter which induces a gene expression by addition of drug. If established is an immortalized liver cell line wherein an expression vector containing both the drug-induced promoter and the site-specific recombinase is integrated into a chromosome, it is not necessary to consider infecting efficiency of virus. If such cell line is used, it is possible to optionally set up the time of the expression of the site-specific recombinase.

The drug-induced promoter is not limited specifically, and well-known promoters such as a tetracyclin induced promoter, a tamoxifen induced promoter and the like can be used. These drug-induced promoters can be selected properly by a person skilled in the art.

Therefore, in the above-mentioned method for proliferating a liver cell in vitro, preferred is that the step of obtaining an immortalized liver cell comprises a step of transferring a cell proliferation factor gene into a mammalian liver cell to obtain an immortalized liver cell, a step of transferring a DNA sequence encoding a site-specific recombinase at the downstream of a drug-induced promoter into the immortalized liver cell, and a step of obtaining an immortalized liver cell which expresses the site-specific recombinase depending on agent.

The liver cell according to the present invention can be used as an assay model for drug metabolism in human liver. A metabolic pathway of a toxic substance and a carcinogen in which environmental pollution thereof and effect thereof on human at use are problems is different between human and other animals. Toxicity and carcinogenicity of a chemical substance including a drug, and an assay of the metabolic pathway in a body has been examined using laboratory animal such as rat, dog or hog. However, since the difference in the metabolic pathway of the chemical substance between human and laboratory animals is obvious, circumspection is required in order to apply the data of experiment on animals to human. Further, from the standpoint of the latest Animal Prevention, it is an important object to develop a means of research wherein experiments using animals are restrained as many times as possible and the change of human condition is studied using human. The liver cell according to the present invention expresses high degree of liver function, and has a significance as a new assay model for drug metabolism which is not a substitute for laboratory animals but has a function closer to that of human liver. Concretely, it is used for 1) analyzing a metabolic system of a drug in a liver, 2) studying interaction of drugs and 3) an assay of production of a mutagenic substance derived from a drug in a liver.

In addition, the liver cell according to the present invention can be used to develop new drug, that is, mass production of a bioactive substance can be performed by cultivating human-derived liver cell line on a large scale. These products include less impurity which are difficult to remove than the bioactive substance produced by yeast, Escherichia coli or clone animals using gene manipulation, therefore, the product can be easily isolated. An application for development of new drug includes production of various kinds of blood coagulation factor, albumin and/or the like.

Furthermore, the liver cell according to the present invention can be used as an infection model of human hepatitis virus. The whole picture of human B type hepatitis virus (HBV) and human C type hepatitis virus (HCV) is becoming clear, but the viruses themselves are not confirmed yet. This is because in vitro culture system is not established yet, which can be a big barrier for fundamental researches such as clarifications of mechanisms of biology and carcinogenesis, for example, replication, particle formation and mutation of virus. It is possible to establish an infective experiment system of HBV and HCV using the liver cell according to the present invention, and then to build a fundamental experiment system for formulating a mechanism of infection, and a strategy for prevention and treatment.

A treating agent for hepatic insufficiency in present invention comprises a liver cell obtained by a method for proliferating a liver cell comprising a step of transferring a cell proliferation factor gene into a mammalian liver cell to obtain an in vitro immortalized liver cell, a step of proliferating the in vitro immortalized liver cell, and a step of removing the cell proliferation factor gene from the in vitro immortalized liver-cell. The treating agent may include other electrolyte, amino acid and glucide in order to protect the liver cell.

As "hepatic insufficiency" in the present invention, there include liver failure such as acute liver failure depending on virus, drug and intoxication (for example, toadstool and the like); liver-based metabolic diseases such as hemophilia, α1-antitrypsin deficiency, galactosemia, hepatorenal tyrosinemia, maple syrup urine disease, glycogenosis type 1a, hepatic porphyria, hypobetalipoproteinemia, hypercholesterolemia, primary hyperoxaluria type 1, Crigler-Najjar syndrome type 1, hyperphenylalaninemia; acute on chronic hepatic insufficiency and the like. It is preferable that the treating agent of the present invention uses for treatments of liver failure and liver-based metabolic diseases.

The dose route of the treating agent in the present invention is preferably intraportal injection, intrasplenic arterial injection or intraperitoneal transplantation. The intraportal injection and the intrasplenic arterial injection are more preferable, the intraportal injection is most preferable. The dosage of the treating agent is at least $1 \times 10^{10}$ cells, preferably $1.5 \times 10^{10}$ cells, more preferably $2.0 \times 10^{10}$ cells.

The artificial liver according to the present invention comprises a liver cell obtained by a method for proliferating a liver cell comprising a step of transferring a cell proliferation factor gene into a mammalian liver cell to obtain an in vitro immortalized liver cell, a step of proliferating the immortalized liver cell, and a step of removing the cell proliferation factor gene from the immortalized liver cell. "Artificial liver" herein is defined as an extracorporeal liver assist device enabling reproduction of precise liver function, wherein an aggregate of functional liver cells based on microporous glucomicrocarrier or other biocompatible supporting matrix such as capillary or ceramics regenerates glucose and urea, sets amino acid disorder in a patient to right together with rapidly neutralization of ammonia and the like being causative agent of hepatic encephalopathy.

The artificial liver according to the present invention may include microcarrier. The microcarrier is useful for increasing the account of the cultured liver cell per unit area as substrate for the liver cell. The microcarrier is preferably spherical dextran, porous resin or collagen microsphere.

In addition, high biocompatible cellulose bead is preferable, and a cellulose bead whole surface is attached with a cell adhesion peptide is more preferable. As the cell adhesion peptide, there include amino acid sequence such as GRGDS (SEQ ID NO: 22) and RGDS (SEQ ID NO: 23) (G: glycine, R: arginine, D: aspartic acid, S: serine), but it is not particularly limited thereto as long as it contains amino acid sequence RGD.

Among the collagen microsphere, a collagen microsphere consisting of only fibrin made of collagen is most preferable, because it can make the culture environment similar to in vivo.

In the present invention, the cellulose bead whose surface is attached with a cell adhesion peptide, and the collagen microsphere consisting of only fibrin made of collagen are preferable from the viewpoint of an occupied rate by depositing the liver cell. The collagen microsphere consisting of only fibrin made of collagen can be prepared by treating bovin dermis with pepsin to make it soluble, purifying and then forming the resultant into beads. In case of the cellulose bead whose surface is attached with a cell adhesion peptide, the occupied rate by depositing liver cell is in 80 to 90%, in case of the collagen microsphere consisting of only fibrin made of collagen, it is in about 100%. Therefore, the collagen microsphere consisting of only fibrin made of collagen is most preferable (see FIG. 4(a) and FIG. 4(b)).

Figure 4A:
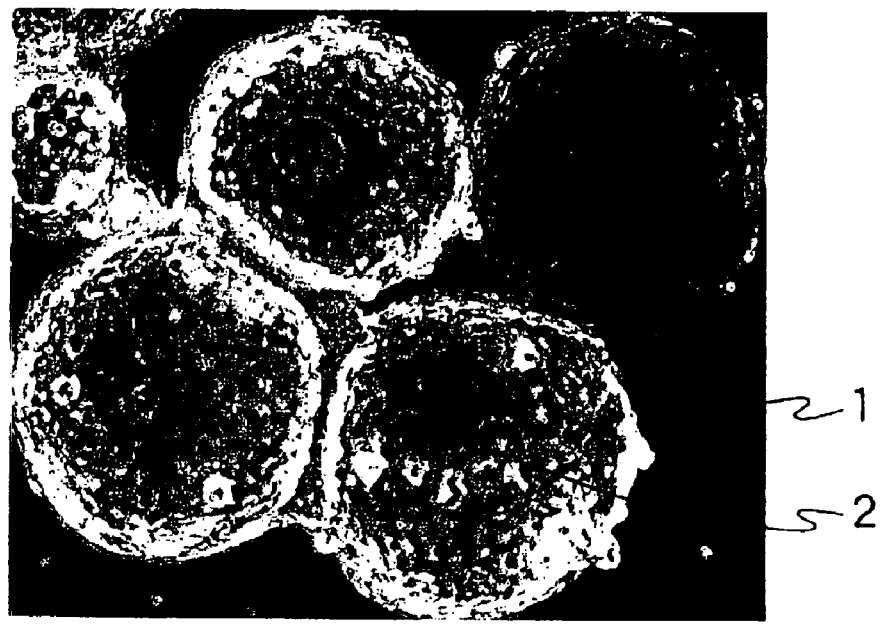
FIG. 4(a) is a microscopic image of hepatocytes adhering to collagen microspheres consisting of only fibrin made of collagen.
Figure 4B:
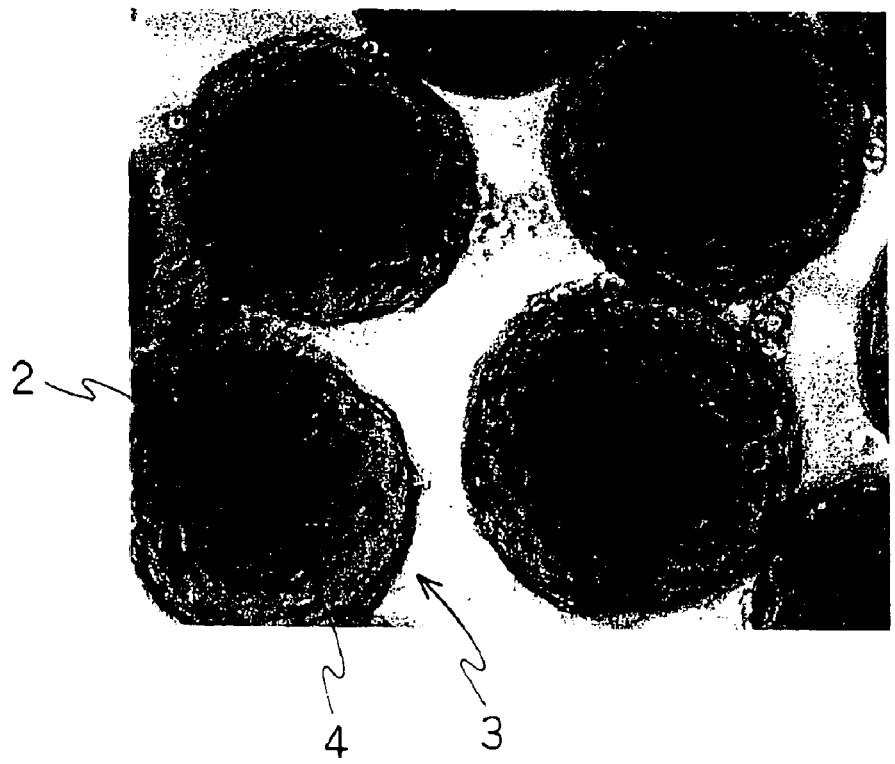
FIG. 4(b) is a microscopic image of hepatocytes adhering to cellulose beads whose surfaces are attached with cell adhesion peptide.

The deposit efficiency of the liver cell on these carriers is explained with FIG. 4(a) and FIG. 4(b). FIG. 4(a) is microgram of liver cells adhering to collagen microsphere consisting of only fibrin made of collagen (commercial number KO-0000-01, available from Funakoshi Co., Ltd.). In FIG. 4(a), it is recognized that collagen microsphere 1 consisting of only fibrin made of collagen is completely covered with the liver cell 2. FIG. 4(b) is microgram of liver cells adhering to the cellulose bead whose surface is attached with a cell adhesion peptide (made by Kuraray Co., Ltd.). In FIG. 4(b), it is observed that the cellulose bead 3 whose surface is attached with a cell adhesion peptide is covered with the liver cell 2 in lower occupied rate than (a), and the surface 4 of bead without adhering cells.

The artificial liver according to the present invention may comprise a vessel in order to store the above liver cells. As the vessel, there include a hollow fiber type, a laminated type wherein cultured liver cells are piled in a module as sort of flat plate, and a type packed with nonwoven fabric, but it is not particularly limited thereto as long as it enables high cell density and functionally maintenance of cultivation for the long term.

The artificial liver according to the present invention may have further a conduit. A portion of plasma containing noxious substrates is separated from the blood derived from a patient through the conduit by plasma separating device. The separated plasma is transferred to circuit of bio-artificial liver module side through the conduit, and in the bio-artificial liver module the noxious substrates is detoxified and glucose and the others are regenerated. The conduit may be also used in order to lead the treated plasma to the patient body. The conduit may be used to connect in series with gas exchange device, activated carbon column and the like in order to supply oxygen to cultured liver cell in the bio-artificial liver module. The bio-artificial liver module is not particularly limited as long as it has inflow route of plasma from a patient and outflow route such that the treated plasma is lead to the patient.

The method of the present invention is valiant treating strategy which dissolves shortage of donor liver. Furthermore, reversible immortalization mechanism according to the present invention can be widely applied to other somatic cell under various treating conditions for the future.

The present invention is further explained in details based on the examples concretely, but is not limited thereto.

PREPARATION EXAMPLE 1

Preparation of Retroviral Vector SSR#197

Retroviral vector SSR#197 (see FIG. 1) was prepared according to the conventional method (K. A. Westerman, et al., Proc. Natl. Acad. Sci., USA., vol 93, 8971, (1996)). Concretely, the process is as follows.

1. LXSN retroviral vector was digested with EcoRI and Rsr2. After mutating the EcoRI derived the backbone vector, a polylinker comprising restriction sites (Not1, BamH1, Hind3, EcoR1, Hpa1, Sal1, Sfi1, Cla1 and Rsr2) was inserted into the resultant. Into the Not1/Hind3 site of the resulting vector, a synthesized 511LoxP sequence was inserted. hTERT gene was inserted into the EcoR1/Sal1 site.

2. A cassette vector comprising IRES-GFP, 511LoxP sequence and hepatitis B posttranscriptional regulatory element (T. S. Yen, Mol Cell Biol., 1995) was prepared as follows.

pUC19 was digested with EcoR1 and Hind3. After mutating the EcoR1 derived the backbone vector, a polylinker comprising restriction sites (Xho1, Sal1, EcoRV, Not1, Hpa1, Hind3, EcoR1, Cla1, Sfi1 and Hind3) was inserted into the resultant. Into the Not1 and Hind3 site of the resulting vector, a synthesized 511LoxP sequence was inserted. And then, prepared was a fragment wherein IRES derived from pCITE-Novagen (available from Novagen) and EGFP gene (available from Clontech Inc) were joined at the Nco1 site and the one terminus was a Sal1 site and the other terminus was a blunted Cla1 site. The fragment was inserted into the Sal1 and blunted Bgl2 site of the backbone vector.

3. SSR# 197 vector was completed by inserting the Xho1-and-Cla1 fragment derived from the cassette vector prepared in the above step 2 into the Sal1-and-Cla1 site of the vector prepared in the above step 1.

EXAMPLE 1

Establishment of Human Adult Immortalized Hepatocyte Line TTNT-1

Crip cells producing retroviral vector SSR#197 (the capacity of the Crip cell to produce retroviral vector SSR#197, i.e. titer, was $1\times10^5$ cfu/ml) were seeded in a flask T-75 at $1\times10^5$ cells/cm$^2$ and then cultured in 15 ml of DMEM+10% NCS (newborn calf serum) medium. When the cell density was about 90%, the medium was exchanged for 10 ml of DMEM+10% NCS medium.

Twenty-four hours after the medium was exchanged, 12 µg/ml of polybrene (available from Sigma) was added to a solution obtained by filtering 2 ml of cultural supernatant of the Crip cells containing retroviral vectors SSR#197 with a 0.45 µm filter. The resulting solution was added in exchange for a medium in which $1\times10^6$ cells of primary human adult hepatocytes (catalogue number CS-ABI-3716, available from Dainippon Pharmaceutical Co., Ltd.) had been cultured, to infect the hepatocytes for 4 hours. The same infecting procedure was performed twice a day for 3 days in total. After the last infection in each day, the medium was exchanged for flesh CS-C medium and then hepatocytes were cultured therein.

Figure 2B:
FIG. 2(b) is a fluorescence microscopic image of the cells shown in FIG. 2(a).
Figure 2D:
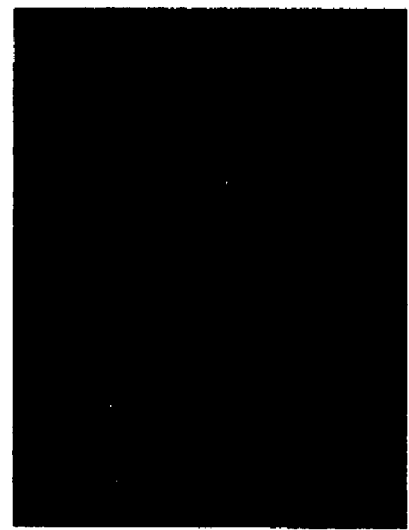
FIG. 2(d) is a fluorescence microscopic image of the cells shown in FIG. 2(c).
Figure 2A:
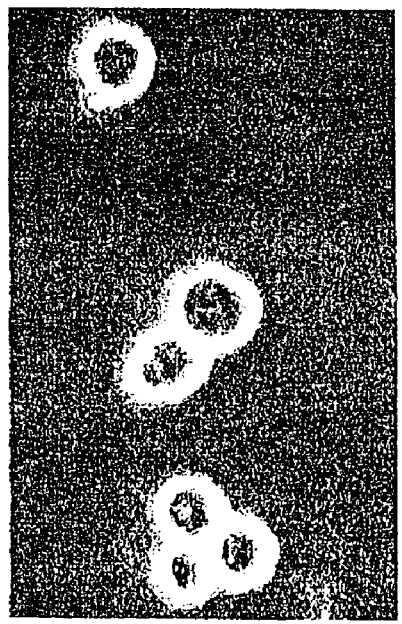
FIG. 2(a) is a phase-contrast microscopic image of hepatocytes infected with retroviral vector SSR#197.

Two days after the final infection, the cells were treated with trypsin and collected. GFP-positive cells were then collected using FACS Calibur (made by Becton Dickinson) (See FIGS. 2(a) and (b)). TTNT-1 was established by the limiting dilution method (seeding at a half cell/well) using CS-C serum free medium kit (catalogue number CS-SF-4ZO-500, available from Dainippon Pharmaceutical Co., Ltd.). The TTNT-1 cells were deposited in International Patent Organism Depositary of National Institute of Advanced Industrial Science and Technology (FERM BP-7498). The TTNT-1 cells are immortalized without a crisis of cease of cell proliferation, grew in one layer in CS-C medium, and then after about 24 hours the number doubled. The TTNT-1 cells showed morphological features of cells having a large nucleus with some nucleoli and rich intracellular granules like a parenchyma cell of a liver.

EXAMPLE 2

Excision of hTERT Gene Using Cre Recombinase (see FIG. 1)

Figure 2C:
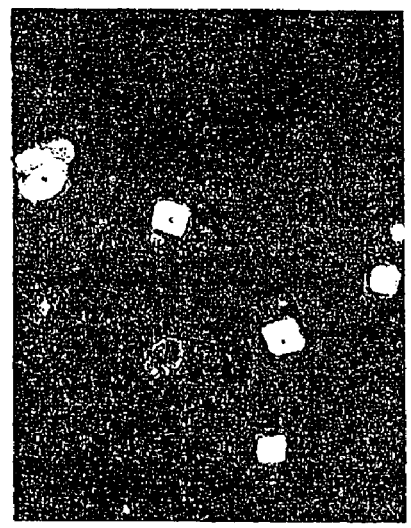
FIG. 2(c) is a phase-contrast microscopic image of hepatocytes treated with adenoviral vector AxCANCre to remove a DNA fragment coded hTERT and GST protein.

The TNNT-1 cells were infected with recombinant adenoviral vectors AxCANCre ($3.3\times10^8$ pfu/ml), which produced Cre recombinase labeled with a nuclear localization signal (NLS) and was unable to make replications (available from Riken Gene Bank, Japan, RDB No. 1748), at MOI (multiplicity of infection)=50. After the infection with AxCANCre for 48 hours, the cells were treated with trypsin and collected, and then only negative cells in which hTERT gene did not express were obtained using FACS Calibur. That was confirmed under a fluorescence microscopy (see FIG. 2(c) and FIG. 2(d)). Further by the RT-PCR method, in the TTNT-1 cells obtained before and after excision of the hTERT gene, expression of genes which were important to metabolism in a liver, i.e. albumin gene, ASGPR gene, bilirubin-UGT gene, CYP3A4 gene, GK gene, GS gene, GST-π gene, human blood coagulation factor X gene and human β-actin gene, and hTERT gene were assayed. In the RT-PCR method, RNA was extracted from the TTNT-1 cells using RNAzol (available from Cinna/BioTecx, Friendswood, Tex., USA) and 2 µg of the resulting total RNA was reverse-transcribed with RNA reverse transcriptase at 22° C. for 10 minutes and then at 42° C. for 20 minutes.

The obtained 2 µg of the reverse transcribed products was applied to PCR amplification using 20 pmol/ml of each primer and AmpliTaq Gold kit (available from Perkin-Elmer/Cetus, Inc., Norwalk, Conn., USA) according to the protocol. PCR was performed as follows: Incubation at 95° C. for 10 minutes, 35 cycle of incubation consisting of 95° C. for 30 seconds, 60° C. for 30 seconds and 72° C. for 30 seconds, and final incubation at 72° C. for 7 minutes. As primer for each gene, the following primers were used.

```
albumin gene
5' primer: AAACCTCTTGTGGAAGAGCC      (SEQ ID NO: 2)
3' primer: CAAAGCAGGTCTCCTTATCG      (SEQ ID NO: 3)

ASGPR gene
5' primer: TAGGAGCCAAGCTGGAGAAA      (SEQ ID NO: 4)
3' primer: ACCTGCAGGCAGAAGTCATC      (SEQ ID NO: 5)

bilirubin-UGT gene
5' primer: ATGACCCGTGCCTTTATCAC      (SEQ ID NO: 6)
3' primer: TCTTGGATTTGTGGGCTTTC      (SEQ ID NO: 7)

CYP3A4 gene
5' primer: CCAAGCTATGCTCTTCACCG      (SEQ ID NO: 8)
3' primer: TCAGGCTCCACTTACGGTGC      (SEQ ID NO: 9)

GK gene
5' primer: ATCAAACGGAGAGGGGACTT      (SEQ ID NO: 10)
3' primer: AGCGTGCTCAGGATGTTGTA      (SEQ ID NO: 11)

GS gene
5' primer: ATGCTGGAGTCAAGATTGCG      (SEQ ID NO: 12)
3' primer: TCATTGAGAAGACACGTGCG      (SEQ ID NO: 13)

GST-π gene
5' primer: GCCCTACACCGTGGTCTATT      (SEQ ID NO: 14)
3' primer: GGCTAGGACCTCATGGATCA      (SEQ ID NO: 15)

human blood coagulation factor X gene
5' primer: GTGCATGGAAGAGACCTGCT      (SEQ ID NO: 16)
3' primer: GAAGTCAAGCAGGTCGAAGG      (SEQ ID NO: 17)

hTERT gene
5' primer: CTGACCAGGGTCCTATTCCA      (SEQ ID NO: 18)
3' primer: TGGTTATCCCAAGCAAGAGG      (SEQ ID NO: 19)

human β-actin gene
                                      (SEQ ID NO: 20)
5' primer: TGACGGGGTCACCCACACTGTGCCCATCTA
                                      (SEQ ID NO: 21)
3' primer: CTAGAAGCATTTGCGGTGGACGATGGAGGG
```

Figure 3A:
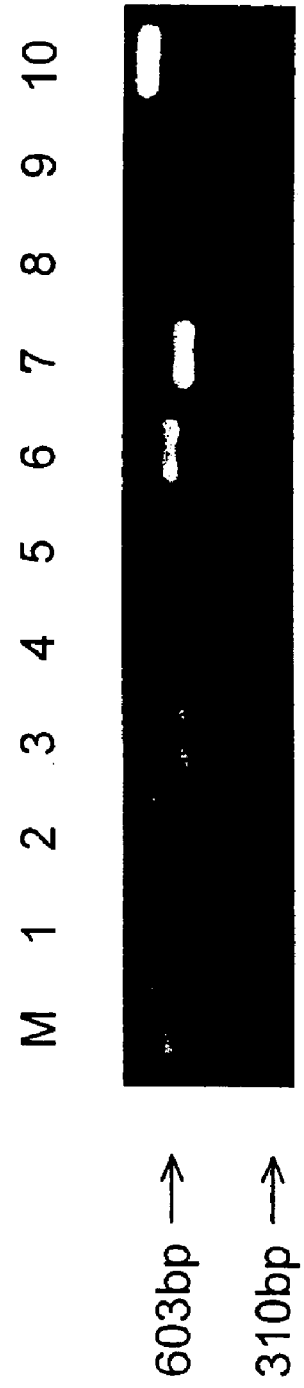
FIG. 3(a) shows the expression of liver specific genes and hTERT gene in TTNT-1 cell before the excision of hTERT gene. Lanes 1 to 9 indicate an expression of albumin gene, asialoglycoprotein receptor (refer to ASGPR hereinafter) gene, liver bilirubin-uridine phosphate glucuronocyl transferase (refer to bilirubin-UGT hereinafter) gene, cytochrome P 450 3A4 (refer to CYP3A4 hereinafter) gene, glucokinase (refer to GK hereinafter) gene, glutamine synthetase (refer to GS hereinafter) gene, glutathione-S-transferase π (refer to GST-π) gene, human blood coagulation factor X (refer to HBCF-X herein after) gene, hTERT gene and human β-actin gene, respectivly. M indcates marker.
Figure 3B:
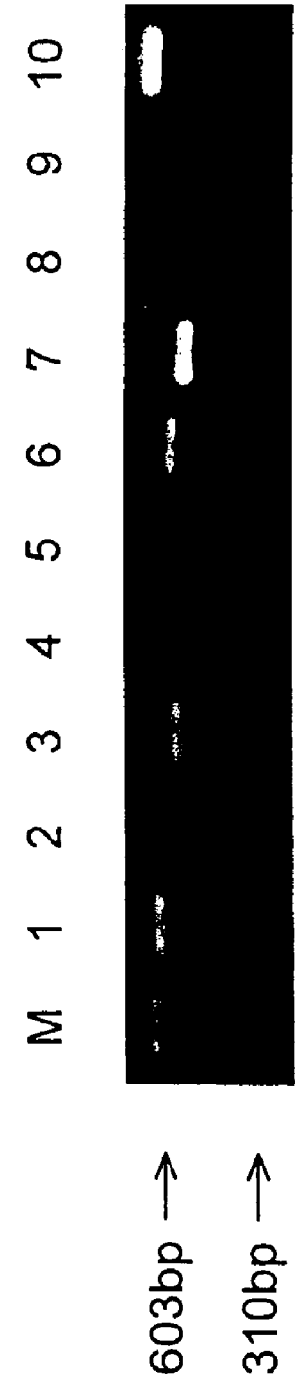
FIG. 3(b) shows the expression of liver specific gene and hTERT gene in TTNT-1 cell after the excision of hTERT gene. Lanes 1 to 9 indicate the expression of the same gene as FIG. 3(a). M indcates marker.

Every one of the above genes obtained showed higher expression level after an excision of hTERT gene according to Cre/LoxP recombination than before the excision (see FIG. 3(a) and FIG. 3(b)).

EXAMPLE 3

The Preparation of Albumin

Using 2 ml of serum free medium CS-C, 1×10⁵ cells of hepatocytes obtained by excising hTERT gene in Example 2 were cultivated for 24 hours at 37° C. Then, 100 μl of the resulting cultural supernatant was collected, and it was used to measure concentration of albumin by using Albuwell (available from EXOCELL INC., Pennsylvana, USA) according to the protocol. As a control, used was the cultural supernatant of hepatocytes which were cultivated in the same way except that 2 ml of DMEM containing 4% fetal calf serum was used as culture medium.

As a result of the measurement, concentration of albumin contained in cultural supernatant was 37.36 μg/dl in case of serum free medium, and 14.6 μg/dl in case of medium containing serum. Therefore, it is shown that albumin can be produced more by using serum free medium.

INDUSTRIAL APPLICABILITY

According to the present invention, a mammalian liver cell line proliferated in large scale can be established using a method for proliferating a liver cell, which comprises the steps of transferring a growth gene into mammalian liver cells to obtain in vitro immortalized liver cells, culturing the in vitro immortalized liver cells, and removing the cell proliferation factor gene from the in vitro immortalized liver cells. TTNT-1 cells used in the present invention have a safety means such as an excision of the cell proliferation factor gene by Cre/LoxP site-specific recombination, so that the patient can avoid a risk of tumor expression in the case of the TTNT-1 transplantation.

Sequence Listing Free Text

SEQ No.1: LoxP sequence

SEQ No.2: 5' primer for polymerase chain reaction to detect Albumin gene

SEQ No.3: 3' primer for polymerase chain reaction to detect Albumin gene

SEQ No.4: 5' primer for polymerase chain reaction to detect ASGPR gene

SEQ No.5: 3' primer for polymerase chain reaction to detect ASGPR gene

SEQ No.6: 5' primer for polymerase chain reaction to detect Bilirubin-UGT gene

SEQ No.7: 3' primer for polymerase chain reaction to detect Bilirubin-UGT gene

SEQ No.8: 5' primer for polymerase chain reaction to detect CYP3A4 gene

SEQ No.9: 3' primer for polymerase chain reaction to detect CYP3A4 gene

SEQ No.10: 5' primer for polymerase chain reaction to detect GK gene

SEQ No.11: 3' primer for polymerase chain reaction to detect GK gene

SEQ No.12: 5' primer for polymerase chain reaction to detect GS gene

SEQ No.13: 3' primer for polymerase chain reaction to detect GS gene

SEQ No.14: 5' primer for polymerase chain reaction to detect GST-π gene

SEQ No.15: 3' primer for polymerase chain reaction to detect GST-π gene

SEQ No.16: 5' primer for polymerase chain reaction to detect human blood coagulation factor X gene SEQ No.17: 3' primer for polymerase chain reaction to detect human blood coagulation factor X gene SEQ No.18: 5' primer for polymerase chain reaction to detect hTERT gene SEQ No.19: 3' primer for polymerase chain reaction to detect hTERT gene SEQ No.20: 5' primer for polymerase chain reaction to detect human β-actin gene SEQ No.21: 3' primer for polymerase chain reaction to detect human β-actin gene SEQ No.22: Cell adhesion peptide SEQ No.23: Cell adhesion peptide

What is claimed is:

1. A method for proliferating a liver cell, which comprises a step of transferring hTERT gene into a mammalian liver cell to obtain an in vitro immortalized liver cell, a step of proliferating the in vitro immortalized liver cell, and a step of removing the hTERT gene from the in vitro immortalized liver cell.

2. The method of claim 1, wherein the mammalian liver cell is a human liver cell.

3. The method of claim 2, wherein the human liver cell is a human adult liver cell.

4. The method of claim 1, wherein the hTERT gene is transferred using a retrovirus vector.

5. The method of claim 1, wherein the hTERT gene is located between a pair of site-specific recombination sequences.

6. The method of claim 5, wherein the pair of site-specific recombination sequences is LoxP sequence.

7. The method of claim 5, wherein GFP gene is present between the pair of site-specific recombination sequences.

8. The method of claim 1, wherein the immortalized liver cell is proliferated in serum-free medium.

9. The method of claim 1, wherein the hTERT gene is removed by a site-specific recombinase from the immortalized liver cell.

10. The method of claim 9, wherein the site-specific recombinase is Cre recombinase.

11. The method of claim 10, wherein Cre recombinase is encoded by an adenoviral vector.

12. A liver cell obtained by a method for proliferating an liver cell comprising a step of transferring a hTERT gene into a mammalian liver cell to obtain a immortalized liver cell, a step of proliferating the in vitro immortalized liver cell, and a step of removing the cell proliferation factor gene from the in vitro immortalized liver cell.

13. The in vitro liver cell of claim 12, if which used as an assay model for drug metabolism in human liver.

14. An agent for treating liver insufficiency, which comprises an in vitro liver cell obtained by a method for proliferating a liver cell comprising a step of transferring hTERT gene into a mammalian liver cell to obtain an in vitro immortalized liver cell, a step of proliferating the in vitro immortalized liver cell, and a step of removing the hTERT gene from the immortalized liver cell.

15. An artificial liver, which comprises a liver cell obtained by a method for proliferating a liver cell comprising a step of transferring a cell proliferation factor gene into a mammalian liver cell to obtain an in vitro immortalized liver cell, a step of proliferating the in vitro immortalized liver cell, and a step of removing the cell proliferation factor gene from the in vitro immortalized liver cell.

16. The artificial liver of claim 15, which contains a microcarrier.

17. The artificial liver of claim 16, wherein the microcarrier is cellulose bead.

18. The artificial liver of claim 17, wherein the cellulose bead is a cellulose bead whose surface is attached with a cell adhesion peptide.

19. The artificial liver of claim 16, wherein the microcarrier is collagen microsphere.

20. The artificial liver of claim 16, wherein cell occupied rate on the microcarrier is in range of 80 to 100%.

21. A method for preparing albumin comprising the step of cultivating an in vitro liver cell in serum free medium, the in vitro liver cell being obtained by the method comprising a step of transferring a cell proliferation factor gene into a mammalian liver cell, a step of proliferating the immortalized liver cell, and a step of removing the cell proliferation factor gene from the immortalized liver cell.

22. The method of claim 1, wherein the step of obtaining an immortalize liver cell comprises a step of transferring a cell proliferation factor gene into a mammalian liver cell to obtain an in vitro immortalized liver cell, a step of transferring a DNA sequence encoding a site-specific recombinase at the downstream of a drug-induced promoter into the in vitro immortalized liver cell, and a step of obtaining an immortalized liver cell which expresses the site specific recombinase depending on agent.

* * * * *